(12) United States Patent
Mathieu et al.

(10) Patent No.: US 6,369,285 B1
(45) Date of Patent: Apr. 9, 2002

(54) PROCESS FOR PREPARING HALOHYDROCARBONS

(75) Inventors: Véronique Mathieu, Wavre (BE); Charles-Marie Anciaux, Tavaux (FR)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/677,127

(22) Filed: Sep. 29, 2000

(30) Foreign Application Priority Data

Oct. 6, 1999 (EP) .............................. 99203270

(51) Int. Cl.⁷ ......................... C07C 21/18; C07C 17/08
(52) U.S. Cl. ................ 570/172; 570/164; 570/165; 570/166; 570/167; 570/168; 570/169
(58) Field of Search .................. 570/172, 164, 570/165, 166, 167, 168, 169

(56) References Cited

U.S. PATENT DOCUMENTS 3,843,734 A    10/1974   Trebillon
5,917,098 A    6/1999    Bertocchio et al.

FOREIGN PATENT DOCUMENTS

| EP | 131 561 | 1/1985 | |
| EP | 787 707 | 8/1997 | |
| FR | 2120337 | 8/1972 | |
| GB | 1146463 | 3/1969 | |
| WO | 97/05090 | * 2/1997 | ................ 570/172 |
| WO | 97/07083 | 2/1997 | |
| WO | 98/50329 | 11/1998 | |
| WO | 98/50330 | 11/1998 | |
| ZA | 98/3775 | 1/2000 | |
| ZA | 98/3781 | 1/2000 | |

* cited by examiner

*Primary Examiner*—Alan Siegel
(74) *Attorney, Agent, or Firm*—Connolly Bove Lodge & Hutz LLP

(57) ABSTRACT

Halohydrocarbons containing at least 3 carbon atoms are obtained by reaction between a haloalkane and an olefin in the presence of a catalyst in a reaction medium which is essentially free of water.

12 Claims, No Drawings

PROCESS FOR PREPARING HALOHYDROCARBONS

The present invention relates to a process for preparing halohydrocarbons containing at least 3 carbon atoms, by catalytic reaction between a haloalkane and an olefin.

The addition of a haloalkane to an olefin is a well-known reaction. However, it is occasionally difficult to control the reaction such that only one olefin molecule adds to one haloalkane molecule (formation of a 1:1 addition product or adduct).

Patent application WO 97/07083 discloses a process for preparing halohydrocarbons under the catalytic action of cuprous chloride in the presence of t-butylamine as co-catalyst. However, in such a process, the yield of telomerization product is quite low.

Patent application EP-A-787 707 discloses a process for preparing 1,1,1,3,3-pentachlorobutane under the catalytic action of cuprous chloride in the presence of co-catalysts of amine type. However, the yield of and selectivity towards telomerization product are not excellent.

The present invention is directed towards providing a telomerization process for preparing halohydrocarbons containing at least 3 carbon atoms, by catalytic reaction between a haloalkane and an olefin, with improved yields and selectivities.

Consequently, the invention relates to a process for preparing halohydrocarbons containing at least 3 carbon atoms, in which a haloalkane and an olefin are reacted in the presence of a catalyst in a reaction medium, in which process the reaction medium is essentially free of water.

Specifically, it has been found, surprisingly, that when a haloalkane and an olefin are reacted in the presence of a catalyst in a reaction medium that is essentially free of water, both the selectivity towards desirable monoadducts of haloalkane and olefin and the conversion of the olefin are increased, which results in a highly efficient production of desirable halohydrocarbons containing at least 3 carbon atoms.

In the process according to the invention, the reaction medium comprises at least the catalyst, the haloalkane and the olefin. The reaction medium can also comprise, for example, a co-catalyst and/or a solvent, preferably a co-catalyst.

The reaction medium generally contains not more than 1300 mg/kg of water. The reaction medium often contains not more than 1000 mg/kg of water. A reaction medium containing not more than 700 mg/kg of water is suitable for use. The reaction medium preferably contains not more than 400 mg/kg of water. A reaction medium containing not more than 300 mg/kg of water is most particularly preferred. Needless to say, the process can be carried out in a totally anhydrous reaction medium. However, it has been found that the presence of traces of water in small amounts is not harmful. Typically, the process according to the invention is carried out with a reaction medium containing more than 20 mg/kg of water, or even more than 50 mg/kg of water.

The water content of the reaction medium can be controlled, for example, by removing the traces of water from the reactor used. It is possible, for example, prior to introducing the reaction medium, to heat the reactor and/or to purge it with a dry gas. Furthermore, the water content in the constituents of the reaction medium can be reduced, for example in the catalyst, the haloalkane and the olefin, and optionally in the co-catalyst and/or the solvent. Operations which can be used to reduce the water content in the constituents of the reaction medium are, for example, a drying operation such as, for example, an adsorption on a solid adsorbent or a distillation operation.

In industrial plants, it is desirable to recycle certain compounds present in the reaction medium at the end of the reaction, into the step in which the olefin and the haloalkane are reacted in the presence of a catalyst.

One variant of the process according to the invention thus relates to a process in which a) at least a fraction of a reaction mixture obtained from the step in which the olefin and the haloalkane are reacted in the presence of a catalyst is subjected to a treatment to reduce the water content; and then b) at least some of the treated fraction is recycled into the step in which the olefin and the haloalkane are reacted.

This variant is particularly useful when at least a fraction of a reaction mixture obtained from the step in which the olefin and the haloalkane are reacted in the presence of a catalyst containing unconsumed reagents is subjected to at least one treatment with an aqueous medium. Where appropriate, the treatment with the aqueous medium is intended in particular to stop the reaction between the olefin and the haloalkane and to separate out the catalyst and optionally the co-catalyst from the other constituents of the reaction medium. In one preferred variant, the co-catalyst is isolated from the aqueous medium by a separation operation such as, for example, a stripping or a distillation and, if necessary, the co-catalyst separated out is subjected to an additional treatment to reduce the water content prior to being recycled into the reaction between the olefin and the haloalkane.

The fraction subjected to the treatment to reduce the water content can contain unconsumed reagents (olefin and/or haloalkane), catalyst, co-catalyst, solvent or mixtures of these compounds. In one preferred variant, it contains olefin. In another preferred variant, it contains co-catalyst. In yet another variant, it contains haloalkane.

The process according to the invention can be a continuous or batchwise process. In a batchwise process, it is preferred to carry out a gradual addition to the reaction medium during the reaction of at least a portion of at least one reagent selected from the olefin and the haloalkane, and optionally the co-catalyst and/or the solvent.

In the process according to the invention, the catalyst can be chosen from the metal derivatives known to catalyse the reaction of a haloalkane with an olefin. Mention is made, for example, of the salts and organic compounds of the metals from groups VIA, VIIA, VIII and IB of the Periodic Table of the Elements. Among these metals, nickel, iron and copper give good results. Copper compounds are suitable as catalyst. Copper salts and organocopper compounds are particularly preferred as catalyst. Such catalysts are described, for example, in patent applications WO-A-98/50329 and WO-A-98/50330, the content of which is incorporated by reference in this respect. Copper (I) chloride, copper (II) chloride or copper (II) acetylacetonate give good results. Hydrated copper salts can be used, providing that they do not introduce into the reaction medium a water content higher than the content specified above.

However, anhydrous copper salts are preferably used. In a particularly preferred manner, an anhydrous copper (II) salt is used. An anhydrous copper (II) salt chosen from copper (II) halides or acetate, in particular anhydrous copper (II) chloride, is particularly suitable.

In the process according to the invention, the reaction is preferably carried out in the presence of a co-catalyst selected, for example, from the group consisting of amines and trialkylphosphine oxides.

An amine is preferably used as co-catalyst, in particular a primary amine. Amines which can be used in particular are t-butylamine and the tert-alkyl amines Primene® 81-R and JM-T sold by Rohm & Haas Company. t-Butylamine and the amines Primene® 81-R and Primene® JM-T are most particularly preferred. The amine Primene® 81-R is a mixture of primary and tert-alkyl amines containing from 12 to 14 carbon atoms. The amine Primene® JM-T is a mixture of primary and tert-alkyl amines containing from 18 to 22 carbon atoms.

Among the trialkylphosphine oxides which can be used as co-catalyst, mention may be made in particular of the compounds of formula (R1R2R3)PO, in which R1, R2 and R3 represent identical or different, preferably linear C3–C10 alkyl groups. Tri(n-butyl)phosphine oxide, tri(n-hexyl) phosphine oxide, tri(n-octyl)-phosphine oxide, n-octyldi(n-hexyl)phosphine oxide and n-hexyldi(n-octyl)phosphine oxide and mixtures thereof are chosen in particular.

The catalyst/co-catalyst system which is preferred in the process according to the invention is the system consisting of a copper compound and a primary amine whose carbon atom neighbouring the $NH_2$ group is a quaternary carbon atom, i.e. a carbon not bearing a hydrogen atom. Catalyst/co-catalyst systems formed from copper (II) acetylacetonate and t-butylamine or from copper (II) chloride and t-butylamine are particularly preferred.

A catalyst/co-catalyst system which is most particularly preferred is the system formed from copper (II) acetylacetonate and Primene® JM-T.

In the process according to the invention, the reaction is preferably performed in the absence of solvent. However, the reaction can also be performed in the presence of a solvent. Any solvent in which the reagents form the desired product in a satisfactory yield can be used.

The haloalkanes used in the process according to the present invention are generally saturated organic compounds. They preferably contain from one to three carbon atoms. They often contain at least two chlorine atoms. Haloalkanes in which at least 2 chlorine atoms are linked to the same carbon atom give good results. Haloalkanes comprising a dichloromethyl or trichloromethyl group are preferred. As examples of haloalkanes according to the present invention, mention may be made of dichloromethane, chloroform, carbon tetrachloride and 1,1,1-trichloroethane. Carbon tetrachloride is most particularly preferred. The haloalkanes can also comprise other substituents such as other halogen atoms, alkyl groups or haloalkyl groups. However, haloalkanes containing only chlorine as halogen are preferred.

The olefin used in the process according to the present invention is generally an ethylene, a propylene or a butene, optionally substituted with a substituent. The substituents are chosen, for example, from halogen atoms, alkyl or haloalkyl groups, nitrile (CN) groups or carboxylic acid (COOH) groups. Haloolefins are particularly suitable. Among the haloolefins, chloroolefins give good results. Chloroolefins which can be used in the process according to the invention generally correspond to the general formula

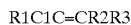   (I)

in which R1, R2 and R3 independently represent an H or Cl atom, a linear, cyclic or branched, optionally substituted alkyl or alkenyl group, or an optionally substituted aryl or heteroaryl group.

Non-limiting examples of chloroolefins which may be mentioned include vinyl chloride, vinylidene chloride, trichloroethylene and various chloropropene isomers such as 1-chloro-1-propene, 2-chloro-1-propene and 3-chloro-1-propene. Excellent results can be obtained with vinyl chloride and 2-chloro-1-propene.

The halohydrocarbons obtained according to the process of the present invention generally belong to the family of chloroalkanes containing at least three carbon atoms. These are often chloropropanes, chlorobutanes or chloropentanes. The carbon atoms in the said chloropropanes, chlorobutanes and chloropentanes can also be substituted with other functional groups such as, for example, alkyl or aryl groups, nitrile (CN) groups or carboxylic acid (COOH) groups. The halohydrocarbons often contain only chlorine as halogen. Chloropropanes and chlorobutanes not substituted with other functional groups are preferred.

The halohydrocarbons obtained according to the process of the present invention preferably correspond to the general formula $C_nH_{(2n+2)-p}Cl_p$ in which n is an integer and takes the values 3 or 4 and p is an integer which takes the values 3 to 7. Examples of compounds obtained according to the process of the present invention are 1,1,1,3,3-pentachloropropane, 1,1,2,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1-dichloro-2-trichloromethylpropane. Among these compounds, 1,1,1,3,3-pentachloropropane, 1,1,1,3,3-pentachlorobutane and 1,1,1,3,3,3-hexachloropropane are preferred. 1,1,1,3,3-Pentachlorobutane and 1,1,1,3,3-pentachloropropane are most particularly preferred.

The reaction medium is maintained at a temperature and pressure that are sufficient to allow the catalytic reaction of the haloalkane with the olefin. The reaction conditions that are preferred in the process according to the invention as regards the temperature, pressure, time and ratio between the constituents of the reaction medium, etc. are disclosed in patent application WO-A-98/50330, the content of which is incorporated by reference.

The halohydrocarbons obtained according to the process of the invention are precursors of the corresponding fluoro analogues, which can be readily obtained by treatment with hydrogen fluoride, which is preferably anhydrous, optionally in the presence of a fluorinating catalyst such as, for example, an antimony salt, a titanium salt, a tantalum salt or a tin salt. The halides are preferred as salt of the said metals. Other fluorinating catalysts which can be used are chosen from the compounds, preferably the oxides, of chromium, of aluminium and of zirconium. Specific examples of fluorohydrocarbons correspond to the formula $C_nH_{(2n+2)-p}F_p$ in which n is an integer and takes the values 3 or 4 and p is an integer which takes the values 3 to 7. Preferred fluorohydrocarbons are chosen from 1,1,1,3,3-pentafluoropropane, 1,1,1,3,3-hexafluoropropane and 1,1,1,3,3-pentafluorobutane.

The invention consequently also relates to a method for obtaining a fluorohydrocarbon, comprising (a) the synthesis of a halohydrocarbon according to the process according to the invention, and (b) a treatment of the halohydrocarbon obtained from (a) with hydrogen fluoride as described above. The examples below are intended to illustrate the invention without, however, limiting it.

EXAMPLES 1–4

1,1,1,3,3-Pentachlorobutane was prepared by reaction between 2-chloro-1-propene (2-CPe) and carbon tetrachloride in the presence of cupric chloride and t-butylamine (tBu) in the presence of variable amounts of water. To do this, the reagents (2-CPe, $CCl_4$), the catalyst ($CuCl_2$) and the amine (tBu) were introduced into a glass penicillin-type flask in 2-CPe/CCl$_4$/CuCl$_2$/tBu molar ratios of 1/2/0.002/0.1 and a certain amount of water was added. The flask was then closed hermetically and placed in an oil bath heated to 80° C. Stirring was provided by a magnetic bar. After reaction for 0.5 h, a sample of liquid was taken by syringe and assayed by a chromatographic method to determine the degree of conversion of the olefin. The results are collated in the table below, along with the selectivity towards 1,1,1,3,3-pentachlorobutane obtained after reaction for 3 hours.

TABLE

| Example | [H$_2$O], mg/kg | Conversion of 2-chloro-1-propene, % | Selectivity towards HCC-360, % |
|---|---|---|---|
| 1 | 249 | 83 | 96.4 |
| 2 | 639 | 60 | 95.6 |
| 3 | 679 | 30 | 91.2 |
| 4 | 1349 | 5 | 73.0 |

EXAMPLE 5

1,1,1,3,3-Pentachlorobutane was prepared by reaction, in substantially anhydrous medium, between 2-chloro-1-propene (2-CPe) and carbon tetrachloride in the presence of copper acetylacetonate and the amine Primene® JM-T (Rohm & Haas). To do this, the reagents (2-CPe, CCl$_4$), the catalyst (Cu(acac)$_2$) and the amine (JM-T) were introduced into a reactor in 2-CPe/CCl$_4$/Cu(acac)$_2$/JM-T molar ratios of 1/2/0.001/0.22. The reactor was then heated to 90° C. After reaction for 2 h, a sample of liquid was taken by syringe and assayed by a chromatographic method to determine the composition of the reaction medium. The degree of conversion of the 2-CPe was 100% and the selectivity towards 1,1,1,3,3-pentachlorobutane was 95%.

What is claimed is:

1. A process for preparing halohydrocarbons containing at least 3 carbon atoms, in which a haloalkane and an olefin are reacted in the presence of a catalyst in a reaction medium, in which process the reaction medium is essentially free of water and contains between 20 mg/kg and 1000 mg/kg of water and
    a) at least a fraction of a reaction mixture obtained from the step in which the olefin and the haloalkane are reacted in the presence of a catalyst is subjected to a treatment to reduce the water content; and then
    b) at least some of the treated fraction is recycled into the step in which the olefin and the baloalkane are reacted.

2. The process according to claim 1, in which the reaction medium contains not more than 700 mg/kg of water.

3. The process according to claim 1, in which the reaction medium contains not more than 400 mg/kg of water.

4. The process according to claim 1, in which the haloalkane and the olefin are also reacted in the presence of a co-catalyst.

5. The process according to claim 1, in which the catalyst is a copper compound.

6. The process according to claim 1, in which the co-catalyst is an amine.

7. The process according to claim 1, in which the olefin is a haloolefin.

8. The process according to claim 7, in which the haloolefin is a chloroolefin corresponding to the general formula R$_1$ClC=CR$_2$R$_3$ in which R$_1$, R$_2$ and R$_3$ independently represent: H, Cl, linear, cyclic or branched, optionally substituted alkyl or alkenyl; optionally substituted aryl or heteroaryl.

9. The process according to claim 1, in which the halohydrocarbon prepared is chosen from 1,1,1,3,3,-pentachloropropane; 1,1,2,3,3,-pentachloropropane; 1,1,1,3,3-pentachlorobutane; 1,1,1,3-tetrachloropropane; 1,1,3,3-tetrachlorobutane; 1,1,1,3,3,3-hexachloropropane and 1,1-dichloro-2-trichloromethylpropane.

10. The process as claimed in claim 1, wherein the reaction medium contains more than 50 mg/kg of water.

11. A method for obtaining a fluorohydrocarbon which comprises the steps
    (a) synthesizing the halohydrocarbon prepared according to the process according to claim 1,
    (b) treating of the halohydrocarbon obtained in step (a) with hydrogen fluoride.

12. A process for manufacturing halohydrocarbons containing at least 3 carbon atoms, comprising
    (a) reacting an olefin reagent and a haloalkane reagent in a substantially anhydrous reaction medium comprising a catalyst and optionally a co-catalyst or a solvent, thereby obtaining a reaction mixture comprising the halohydrocarbon containing at least 3 carbon atoms, unconsumed reagents, catalyst and optionally co-catalyst,
    (b) subjecting at least a fraction of said reaction mixture to at least one treatment with an aqueous medium,
    (c) subjecting a second fraction obtained from the treatment (b), which comprises at least one compound selected from unconsumed reagents, catalyst, cocatalyst and solvent to a treatment to reduce the water content of said second fraction, thereby obtaining a third fraction,
    (d) recycling at least some of said third fraction to step (a), while maintaining in the reaction medium of step (a) a water content between 20 mg/kg and 1000 mg/kg.

* * * * *

UNITED STATES PATENT AND TRADEMARK OFFICE
CERTIFICATE OF CORRECTION

PATENT NO. : 6,369,285 B1 Page 1 of 1
DATED : April 9, 2002
INVENTOR(S) : Veronique Mathieu It is certified that error appears in the above-identified patent and that said Letters Patent is hereby corrected as shown below:

<u>Column 5,</u>
Line 46, delete "baloalkane" and insert -- haloalkane --.

Signed and Sealed this

Eleventh Day of June, 2002

*Attest:*

*Attesting Officer*

JAMES E. ROGAN
*Director of the United States Patent and Trademark Office*